United States Patent
Schena (10) Patent No.: US 10,433,923 B2
(45) Date of Patent: *Oct. 8, 2019

(54) ROBOTIC ARM WITH FIVE-BAR SPHERICAL LINKAGE

(71) Applicant: INTUITIVE SURGICAL OPERATIONS, INC., Sunnyvale, CA (US)

(72) Inventor: Bruce M. Schena, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1442 days.

This patent is subject to a terminal disclaimer.

(21) Appl. No.: 13/902,734

(22) Filed: May 24, 2013

(65) Prior Publication Data

US 2013/0255425 A1    Oct. 3, 2013

Related U.S. Application Data

(60) Division of application No. 13/431,894, filed on Mar. 27, 2012, now Pat. No. 8,506,556, which is a continuation of application No. 11/623,281, filed on Jan. 15, 2007, now Pat. No. 8,162,926.

(60) Provisional application No. 60/786,491, filed on Mar. 28, 2006, provisional application No. 60/762,233, filed on Jan. 25, 2006.

(51) Int. Cl.
*A61B 34/30* (2016.01)
*A61B 34/00* (2016.01)
*A61B 34/37* (2016.01)
*A61B 90/00* (2016.01)

(52) U.S. Cl.
CPC ............ *A61B 34/70* (2016.02); *A61B 34/30* (2016.02); *A61B 34/37* (2016.02); *A61B 90/361* (2016.02); *Y10T 74/2036* (2015.01); *Y10T 74/20305* (2015.01)

(58) Field of Classification Search
CPC ...................................................... A61B 34/00
USPC .................... 606/1, 130; 74/490; 173/213
See application file for complete search history.

(56) References Cited

U.S. PATENT DOCUMENTS

| 4,496,279 A | 1/1985 | Langer |
| 5,301,566 A | 4/1994 | Tahmasebi et al. |
| 5,397,323 A | 3/1995 | Taylor et al. |

(Continued)

FOREIGN PATENT DOCUMENTS

| EP | 0595291 | 5/1994 |
| JP | S60167785 A | 8/1985 |

(Continued)

OTHER PUBLICATIONS

Partial European Search Report for Application No. 16153176.9, dated Jun. 16, 2016, 7 pages.

(Continued)

*Primary Examiner* — Lynsey C Eiseman (57) ABSTRACT

A robotic arm for a minimally invasive surgical system includes a parallel spherical five-bar linkage adapted to spherically rotationally move a robotic surgical tool coupled to the parallel five-bar spherical linkage about a remote center of spherical rotation. The five-bar spherical linkage is posed in only a range of compact poses. A constraint limits the parallel five-bar spherical linkage to only the range of compact poses.

14 Claims, 8 Drawing Sheets

(56) References Cited

U.S. PATENT DOCUMENTS

| | | | |
|---|---|---|---|
| 5,399,951 | A | 3/1995 | Lavallee et al. |
| 5,582,617 | A | 12/1996 | Kiernan et al. |
| 5,800,423 | A | 9/1998 | Jensen |
| 5,833,656 | A | 11/1998 | Smith et al. |
| 5,966,991 | A | 10/1999 | Gosselin et al. |
| 6,024,576 | A | 2/2000 | Bevirt et al. |
| 6,154,198 | A | 11/2000 | Rosenberg |
| 6,355,048 | B1* | 3/2002 | Hong ............... A61B 90/50 606/107 |
| 6,406,472 | B1 | 6/2002 | Jensen |
| 6,424,885 | B1 | 7/2002 | Niemeyer et al. |
| 6,684,129 | B2 | 1/2004 | Salisbury, Jr. et al. |
| 6,903,721 | B2 | 6/2005 | Braun et al. |
| 6,946,812 | B1 | 9/2005 | Martin et al. |
| 7,108,688 | B2 | 9/2006 | Jensen |
| 8,142,420 | B2 | 3/2012 | Schena |
| 8,162,926 | B2 | 4/2012 | Schena |
| 8,167,872 | B2 | 5/2012 | Schena |
| 8,167,873 | B2 | 5/2012 | Schena |
| 8,469,945 | B2 | 6/2013 | Schena |
| 8,506,556 | B2 | 8/2013 | Schena |
| 2002/0082612 | A1 | 6/2002 | Moll et al. |
| 2003/0023346 | A1 | 1/2003 | Salisbury et al. |
| 2004/0024385 | A1 | 2/2004 | Stuart |
| 2004/0024387 | A1* | 2/2004 | Payandeh ............. A61B 90/11 606/1 |
| 2005/0119638 | A1 | 6/2005 | Jensen |
| 2005/0183532 | A1 | 8/2005 | Najafi et al. |
| 2006/0243085 | A1* | 11/2006 | Hannaford ........... B25J 17/0266 74/490.01 |
| 2007/0173977 | A1 | 7/2007 | Schena |
| 2012/0184968 | A1 | 7/2012 | Schena |
| 2013/0338434 | A1 | 12/2013 | Schena |

FOREIGN PATENT DOCUMENTS

| | | |
|---|---|---|
| JP | H06261911 A | 9/1994 |
| JP | H10512983 A | 12/1998 |
| WO | WO9622591 | 7/1996 |
| WO | WO2007120952 A3 | 10/2007 |
| WO | WO20070114975 A3 | 10/2007 |

OTHER PUBLICATIONS

Extended European Search Report for Application No. 16153176.9, dated Sep. 28, 2016, 10 pages.

Applicant Initiated Interview Summary dated Oct. 27, 2011 for U.S. Appl. No. 11/623,292, filed Jan. 15, 2007.

Applicant Initiated Interview Summary dated Oct. 28, 2011 for U.S. Appl. No. 11/623,281, filed Jan. 15, 2007.

Applicant Initiated Interview Summary dated Oct. 28, 2011 for U.S. Appl. No. 11/623,310, filed Jan. 15, 2007.

Applicant Initiated Interview Summary dated Oct. 28, 2011 for U.S. Appl. No. 11/623,311, filed Jan. 15, 2007.

Applicant Initiated Interview Summary dated Oct. 31, 2011 for U.S. Appl. No. 11/623,305, filed Jan. 15, 2007.

Non-Final Office Action dated Aug. 9, 2012 for U.S. Appl. No. 13/431,894, filed Mar. 27, 2012.

Hannaford, Blake et al. "Novel Control System for Robotic Devices via USB," 1 page (plus 1 page enlargement), Internet http://hawkeye1.net/Projects/BRL_FHD3.1_poster_final.pdf.

University of Washington, "Mini Robot Design for Military Telesurgery in the Battlefield—Braking [sic] the Size Barrier for Surgical Manipulators," BioRobotics Laboratory > Surgical Technology > Device, Internet http://brl.ee.washington.edu/Research_Active/Surgery/Project_07/Project_07.html.

U.S. Appl. No. 11/623,281 Office Action dated Jul. 8, 2011, 19 pages.

U.S. Appl. No. 11/623,292 Office Action dated Jun. 23, 2011, 21 pages.

U.S. Appl. No. 11/623,310 Office Action dated Jul. 12, 2011, 12 pages.

U.S. Appl. No. 11/623,311 Final Office Action dated Aug. 26, 2011, 11 pages.

U.S. Appl. No. 11/623,311 Office Action dated Feb. 1, 2011, 11 pages.

U.S. Appl. No. 11/623,305 Office Action dated Jul. 12, 2011, 28 pages.

Wang, Yuan-Fang, et al.; Choreographed Scope Maneuvering in Robotically-Assisted Laparoscopy with Active Vision Guidance; Proceedings of the 3rd IEEE Workshop on Applications of Computer Vision, 6 pages, 1996, IEEE.

Chinzei, Kiyoyuki, et al., MR Compatible Surgical Assist Robot: System Integration and Preliminary Feasibility Study; in Proceedings of Third International Conference on Medical Imaging and Computer Assisted Surgery (MICCAI), p. 921-930, vol. 1935, Oct. 2000. http://splweb.bwh.harvard.edu:8000, undated, pp. 1-10.

Frisoli, Antonio, et al., Mechanical Design and Kinematic Optimization of a Novel Six-Degree-of-Freedom Parallel Mechanism; http://percro.sssup.it/~antony/research/desktop/6_dof.htm, Pisa, Italy, 11 pages, 1999.

Grace, Kenneth W., "Kinematic Design of an Ophthalmic Surgery Robot and Feature Extracting bilateral Manipulation", Northwestern University, Doctoral Dissertation, Jun. 1995, pp. 1-85.

Rosen, Jacob , et al., "Spherical Mechanism Analysis of a Surgical Robot for Minimally Invasive Surgery—Analytical and Experimental Approaches", Medicine Meets Virtual Reality 13, IOS Press, Jan. 2005, pp. 422-428.

Hunter, J. W., et al., "Ophthalmic Microsurgical Robot and Associatged Virtual Environment", Pergamon, 1995, pp. 173-182.

Lai, Rjui , et al., "Evaluating Control Modes for Constrained Robotic Surgery", IEEE, San Francisco, CA, Apr. 2000, 7 pages.

Lum, Mitchell J., et al., "Hybrid Analysis of a Spherical Mechanism for a Minimally Invasive Surgical (MIS) Robot—Design Concepts for Multiple Optimizations", University of Washington Departments of Electrical Engineering, Mechanical Engineering and Surgery, Seattle, WA, IOS Press 2003, pp. 1-6.

Lum, Mitchell J., "Kinematic Optimization of a 2-DOF Spherical Mechanism for a Minimially Invasive Surgical Robot", University of Washington, Department of Electrical Engineering, Seattle, WA, 2004, pp. i-59.

Lum, Mitchell , et al., "Kinematic Optimization of a Spherical Mechanism for a Minimally Invasive Surgical Robot", http://brl.ee.washington.edu, Seattle, WA, Apr. 2004 IEEE, pp. 829-834.

Lum, Mitchell J., et al., "Multidisciplinary Approach for Developing a New Minimally Invasive Surgical Robotic System", University of Washington Departments of Electrical Engineering, Mechanical Engineering and Surgery, Seattle, WA, Feb. 2006, 6 pages.

Lum, Mitchell , et al., "Optimization of a Spherical Mechanism for a Minimially Invasive Surgical Robot: Theoretical and Experimental Approaches", IEEE Transactions on Biomedical Engineering, vol. 53, No. 7, Jul. 2006, pp. 1440-1445.

Lum, Mitchell, Quantitative Performance Assessment of Surgical Robot Systems: TeleRobotic FLS, University of Washington, 2008.

Vertut, Jean and Coeffet, Philippe Coiffet; "Robot Technology; vol. 3A Teleoperation and Robotics Evolution and Development"; 1986; Prentice-Hall, Inc.; Englewood Cliffs, N.J.

Taylor, Russel H. and Dan Stoianovici, "Medical Robotics in Computer-Integrated Surgery," IEEE Transactions on Robotics and Automation, vol. 19, No. 5, Oct. 2003, pp. 765-781.

Westwood, James D. et al. (Eds.), "Medicine Meets Virtual Reality 13: The Magical Next Becomes the Medical Now", IOS Press, Amsterdam, 2005.

Nagy, Istvan , et al., "The Endo[PA]R System for Minimally Invasive Robotic Surgery", Technische Universitat Munchen, Dec. 2003, pp. 1-22.

PCT/US07/60950 Written Opinion of the International Search Authority, dated Jul. 29, 2008, 9 pages.

PCT/US07/60948 Written Opinion of the International Search Authority, dated Jul. 29, 2008, 8 pages.

PCT/US07/60948 International Search Report, dated Mar. 28, 2008.

(56) References Cited

OTHER PUBLICATIONS

PCT/US07/60950 International Search Report, dated Feb. 2, 2008.

* cited by examiner

ROBOTIC ARM WITH FIVE-BAR SPHERICAL LINKAGE

CROSS REFERENCE TO RELATED APPLICATIONS

This application is a divisional of application Ser. No. 13/431,894, which is a continuation of application Ser. No. 11/623,281, filed Jan. 15, 2007, which claims the benefit pursuant to 35 U.S.C. 119(e) of U.S. Provisional Application No. 60/786,491, filed Mar. 28, 2006, and U.S. Provisional Application No. 60/762,233, filed Jan. 25, 2006, each of which is hereby incorporated by reference in its entirety.

BACKGROUND

Field

The embodiments of the invention relate generally to robotic surgical systems. More particularly, the embodiments of the invention relate to linkage in robotic arms.

Background

Minimally invasive surgery (MIS) provides surgical techniques for operating on a patient through small incisions using a camera and elongate surgical instruments introduced to an internal surgical site, often through trocar sleeves or cannulas. The surgical site often comprises a body cavity, such as the patient's abdomen. The body cavity may optionally be distended using a clear fluid such as an insufflation gas. In traditional minimally invasive surgery, the surgeon manipulates the tissues using end effectors of the elongate surgical instruments by actuating the instrument's handles while viewing the surgical site on a video monitor.

A common form of minimally invasive surgery is endoscopy. Laparoscopy is a type of endoscopy for performing minimally invasive inspection and surgery inside the abdominal cavity. In standard laparoscopic surgery, a patient's abdomen is insufflated with gas, and cannula sleeves are passed through small (generally ½ inch or less) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by a tool shaft. As used herein, the term "end effector" means the actual working part of the surgical instrument and can include clamps, graspers, scissors, staplers, image capture lenses, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in other types of surgeries such as arthroscopy, retroperitoneoscopy, pelviscopy, nephroscopy, cystoscopy, cisternoscopy, sinoscopy, hysteroscopy, urethroscopy, and the like.

BRIEF SUMMARY

The embodiments of the invention are summarized by the claims that follow below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DETAILED DESCRIPTION

The detailed description describes the invention as it may be used in a laparoscopic surgery. It is to be understood that this is merely one example of the types of surgeries in which the invention may be used. The invention is not limited to laparoscopy nor to the particular structural configurations shown which are merely examples to aid in the understanding of the invention. Traditional minimally invasive surgery requires a high degree of surgical skill because the surgeon's hand movements are controlling a surgical tool at a substantial distance from the surgeon's hands, often requiring unnatural and non-intuitive hand motions. In robotically assisted surgery, a surgeon may operate a master controller to control the motion of surgical instruments at the surgical site. Servo mechanisms may move and articulate the surgical instrument based on the surgeon's manipulation of the hand input devices. The robotic assistance may allow the surgeon to control the motion of surgical instruments more easily and with greater precision.

Figure 1:
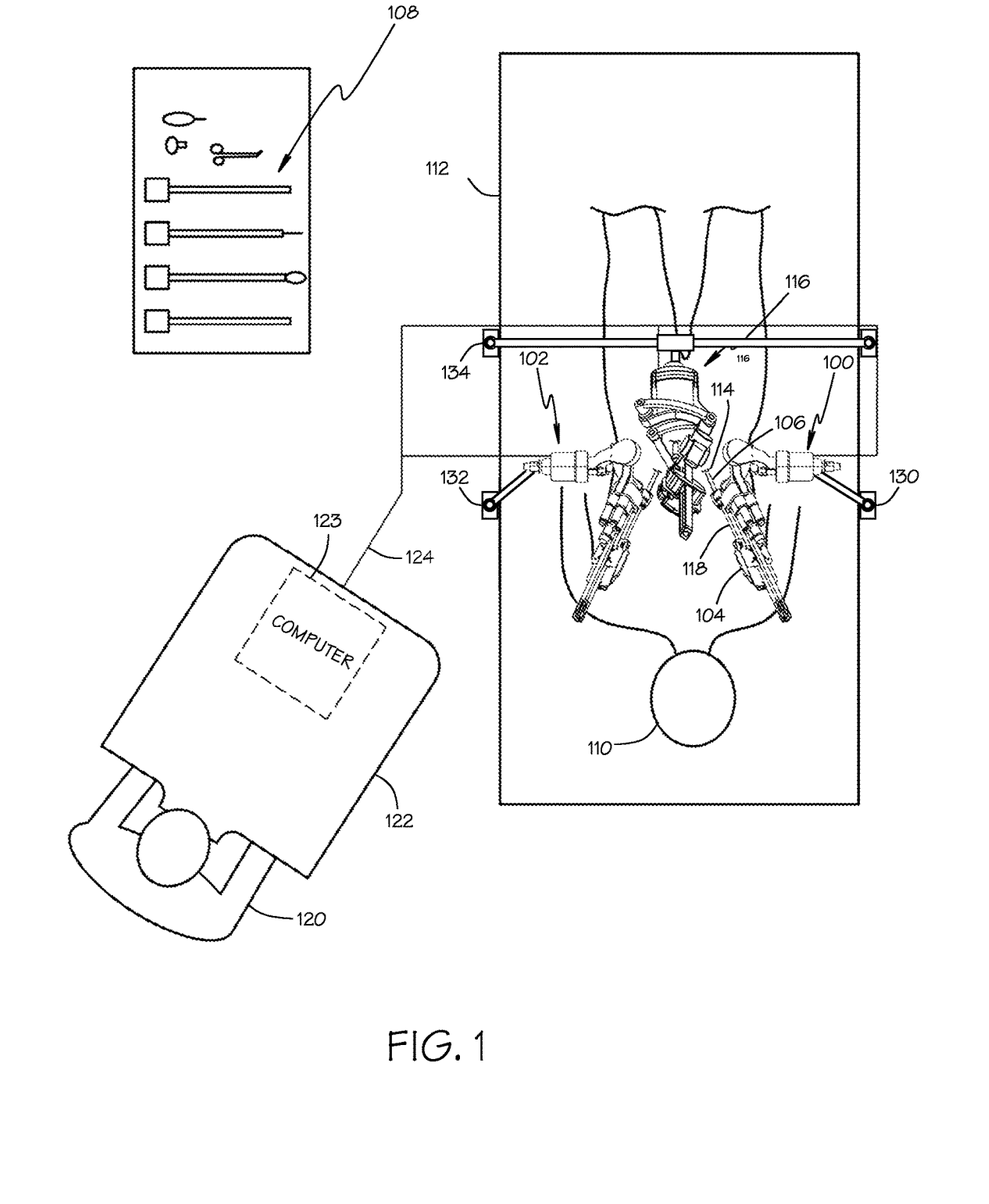
FIG. 1 is a plan view of a surgical suite in which embodiments of the invention are used.

FIG. 1 shows a schematic plan view of a surgical suite in which the invention may be used. A patient 110 is shown on an operating table 112 undergoing robotically assisted laparoscopic surgery. A surgeon 120 may use a master controller 122 to view a video image of the internal surgical site and control one or more surgical instruments and a laparoscopic camera by means of robotic servo mechanisms. The master controller 122 will typically include one or more hand input devices (such as joysticks, exoskeletal gloves, or the like) which are coupled by a servo mechanism to a surgical instrument.

One or more robotic arms 100, 102 that embody the invention may be used to support and move surgical instruments 104 at the surgical site during robotically assisted surgery. It is desirable to support the surgical instrument such that the tool shaft 118 of the instrument pivots about a center of spherical rotation positioned in space along the length of the tool shaft. An additional robotic arm 116 may support and move the laparoscopic camera. The robotic arm 116 for supporting the camera is of a different form than the robotic arms 100, 102 for supporting the surgical instruments 104.

Each robotic arm 100, 102, 116 may be supported by an articulated set-up arm 130, 132, 134. The set-up arms may be attached to the operating table 112. Each set-up arm may include a number of segments coupled by joints that provide one or more degrees of freedom that allow the robotic arm to be positioned within a defined range of motion. One or more locking mechanisms may be provided to fix the segments and joints of the set-up arm when the robotic arm is in the desired position. The set-up arms may allow the robotic arms 100,102 to be fixed at an arbitrary position with respect to the operating table and the patient thereon. Joint angle sensors may be provided on the set-up arm to allow the pose of the set-up arm and the resulting position of the supported robotic arm to be determined.

Each robotic arm 100, 102 may be fixed at a position where the center of spherical rotation is substantially at the access point 114 to the internal surgical site (for example, with the incision that provides entry for the trocar or cannula 106 at the abdominal wall during laparoscopic surgery). An end effector of the surgical instrument 104 supported by the robotic arm 100 can be positioned safely by moving the proximal end of the tool shaft 118 with the robotic arm 100 without imposing dangerous forces against the abdominal wall.

Each robotic arm 100, 102 will support one surgical instrument which may be detachable from the robotic arm. A variety of surgical instruments 108 may replace the surgical instrument 104 on the robotic arm 100 during the course of a single surgery. Each robotic arm 100 may support a cannula 106 that passes through an incision 114 into the body of the patient 110. The tool shaft 118 of the surgical instrument 104 passes through the cannula 106 to the internal surgical site.

The robotic arm 100 may support the surgical instrument 104 such that the cannula 106 and the tool shaft 118 of the instrument pivot about a center of spherical rotation positioned in space along the length of the cannula 106. The center of spherical rotation may also be called the remote center of spherical rotation because it is the spherical center of rotational motion for the robotic arm while being spaced apart from the structure of the robotic arm. Motion about the center of spherical rotation may be described as spherical motion because a point at a radial distance from the center of spherical rotation will move on a spherical surface having the radial distance as its radius. The cannula 106 defines an insertion axis that passes through an access point, such as an incision 114 in the abdominal wall of the patient 110, to the internal surgical site. The tool shaft 118 extends along the insertion axis.

Each robotic arm 100, 102, 116 may include one or more servo motors to move the arm to a desired position. Each robotic arm may include one or more additional servo motors to move the surgical instrument 104 and/or an end effector on the surgical instrument. One or more control cables 124 may provide signals between the computer 123 in the master controller 122 and the servo motors of the robotic arms 100, 102, 116. The master controller 122 may include a computer 123 to provide signals that control the servo mechanisms of the robotic arms and the surgical instruments based on the surgeon's input and received feedback from the servo mechanisms.

Figure 2:
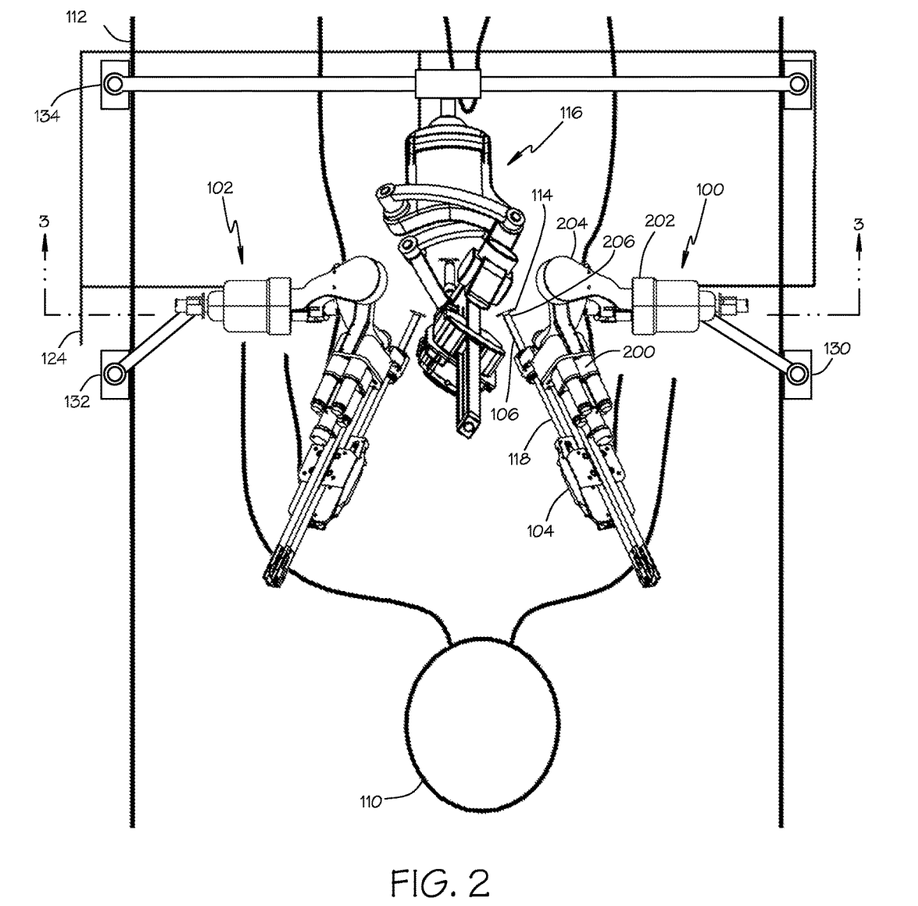
FIG. 2 is a plan view of a portion of the operating suite of FIG. 1.
Figure 3:
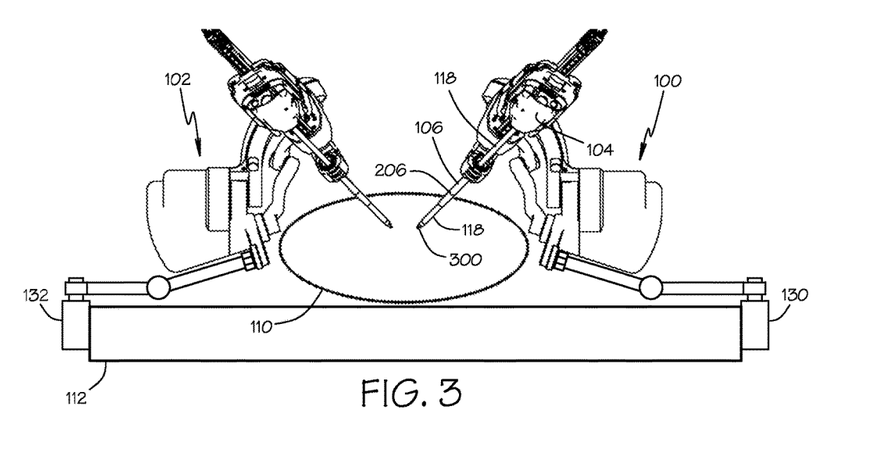
FIG. 3 is a cross-section view along line 3-3 in FIG. 2.

FIG. 2 shows an enlarged view of a portion of FIG. 1 including the patient 110 and the robotic arms 100, 102, 116. FIG. 3 shows an end view of the robotic arms 100, 102 looking from the patient's head toward the feet. A schematic cross-section of the patient 110 is shown in the area where the cannula 106 is inserted. The tool shaft 118 of the surgical instrument 104 may be seen emerging from the end of the cannula 106 internal to the patient 110. An end effector 300 at the internal end of the tool shaft 118 may provide any of a variety of surgical tools which may be actuated by servo mechanisms 200 (shown in FIG. 2) which may be supported by the robotic arm 100.

Figure 4:
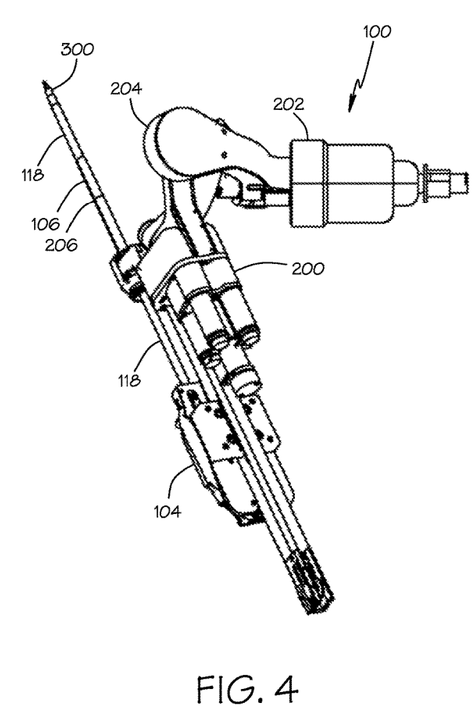
FIG. 4 is a plan view of an embodiment of the invention.
Figure 5:
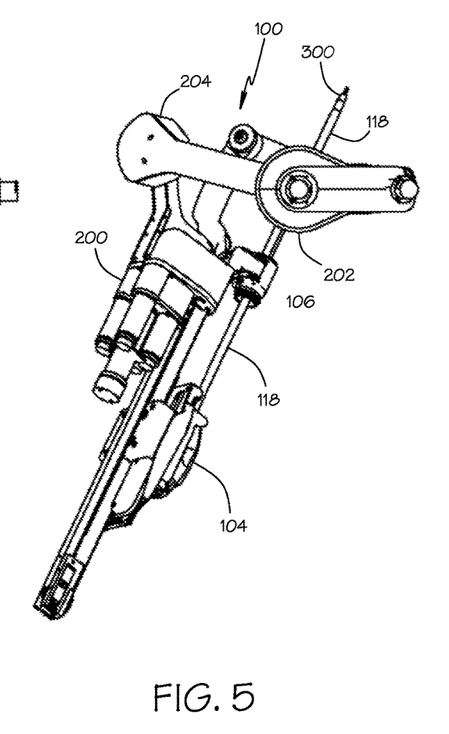
FIG. 5 is a side view of the embodiment of the invention shown in FIG. 4.
Figure 6:
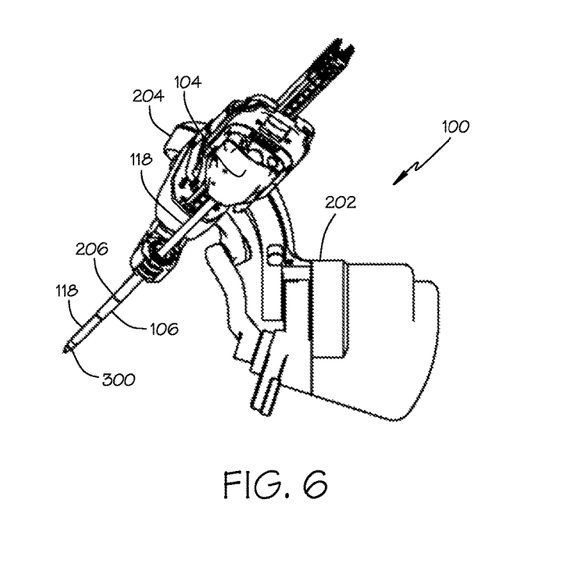
FIG. 6 is an end view of the embodiment of the invention shown in FIG. 4.

A specific position assumed by a robotic arm may be referred to as a pose. Placing a robotic arm in a specific position may be referred to as posing the robotic arm. FIGS. 4, 5, and 6 are orthogonal views of the robotic arm 100 used on the patient's right hand side in the same pose as shown in FIGS. 1-3. FIG. 4 is a plan view. FIG. 5 is a side view. FIG. 6 is an end view.

Referring again to FIGS. 2 and 3, the robotic arm 100, 102 includes a spherical linkage to support the surgical instrument 104, as will be discussed in greater detail below. The spherical linkage constrains the motion of the insertion axis to rotation about a remote center of spherical rotation 206 which may be located along the length of the cannula 106. By locating the remote center of spherical rotation 206 at or near the incision 114, the insertion axis may be moved without significant motion at the incision.

The end effector 300 is passed through the cannula 106 to the internal surgical site along the insertion axis. The end effector 300 is supported by the tool shaft 118 and coupled to servo mechanisms 200 through the tool shaft. The servo mechanisms 200 may manipulate the end effector 300 and may allow a variety of motions which may include rotation about the insertion axis and translation along the insertion axis. Translation of the end effector 300 may be accomplished by translation of the surgical instrument 104 with the tool shaft 118 and attached end effector.

The end effector 300 may be moved in two additional dimensions by moving the tool shaft 118 about its remote center of spherical rotation 206. The robotic arm 100 will control these two dimensions of motion by moving the tool shaft 118 to change its angular position in space. The motion of the tool shaft 118 may be described in terms of the position of the insertion axis in a spherical coordinate system. A point in space may be specified in terms of two angles and a distance from a center of a spherical coordinate system. It will be appreciated that only the two angles are necessary to specify an insertion axis that passes through the center of the spherical coordinate system.

The robotic arm 100 of the present invention includes a parallel spherical five-bar linkage to move and support the surgical instrument 104 such that the tool shaft 118 of the instrument pivots about a remote center of spherical rotation 206 positioned in space along the insertion axis and generally along the length of the cannula 106.

Figure 7:
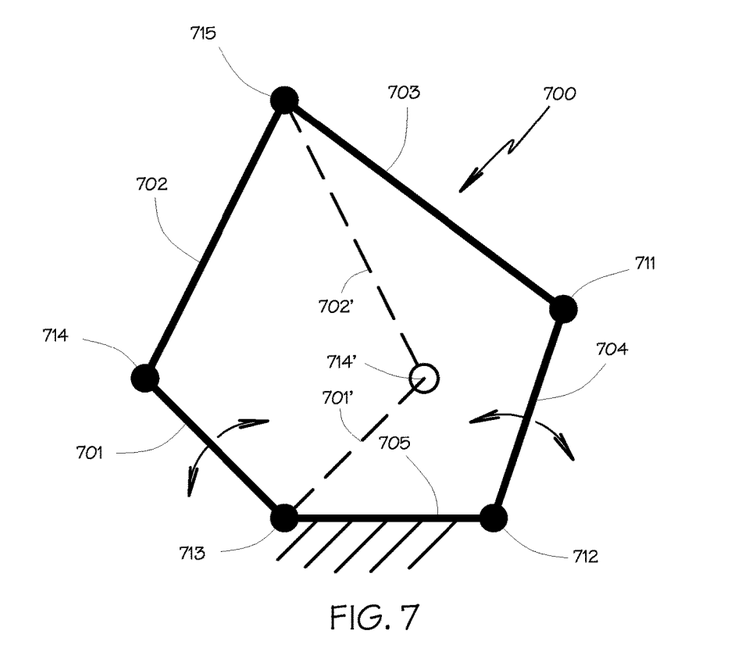
FIG. 7 is a schematic view of a parallel five-bar linkage.

FIG. 7 shows a simplified, 2-dimensional schematic diagram of a parallel five-bar linkage 700. This example illustrates the linkage operating in essentially a flat plane. The inventive linkage operates similarly in 3-dimensional space and will be described subsequently. A parallel five-bar linkage is a system of four rigid bars or links 701, 702, 703,

704 pivoted to each other and to a fixed base link 705. The fixed base link may be referred to as the ground link. It is to be understood that the ground link 705 is fixed only in the sense that it provides a fixed frame of reference for the remaining four links. The ground link 705 may be positioned in space to move the entire five-bar linkage.

Each link includes two pivot axes. The two pivot axes 712, 713 of the ground link may be coincident thereby creating a zero length ground link. The remaining four links all have a substantial distance between the two pivot axes on each link. All of the pivot axes 711, 712, 713, 714, 715 are perpendicular to a common surface. The links are coupled at the pivot axes such that the links can rotate relative to each other about the pivot axis at which they are coupled. The rotatable coupling of the links at a pivot axis can take any of a variety of forms that limits the motion of the coupled links to rotation about the pivot axis. A number of axes are described for the parallel spherical five-bar linkage. The term "axis" may be used interchangeably to refer to a "joint" or a "pivot" except for the insertion axis.

The ground link 705 provides two inboard axes 712, 713. An inboard link 701, 704 is pivotally coupled to each of the inboard axes 713, 712. Each inboard link 701, 704 has an intermediate axis 714, 711 spaced apart from the inboard axis 713, 712. Each inboard link 701, 704 is pivotally coupled to an outboard link 702, 703 at the intermediate axis 714, 711. Each outboard link 702, 703 has an outboard axis 715 spaced apart from the intermediate axis 714, 711. The two outboard links 702, 703 are pivotally coupled at their outboard axes 715. The outboard axis 715 can be positioned perpendicular to the common surface (in this 2-dimensional illustrative example) anywhere within its range of motion thus providing an endpoint motion at the outboard axis 715 with two degrees of freedom. If motors are provided to rotate each of the inboard links 701, 704 about their inboard axis 713, 712, as suggested by the arrows, the outboard axis 715 may be positioned anywhere within its range of motion by rotating the two inboard links with the motors. Conversely, movement of the outboard axis 715 within its range of motion translates into rotation of the two inboard links 701, 704 about their inboard axis 713, 712.

A linkage that couples rotation of two ground-referenced independent links with two dimensional movement of an axis is a parallel linkage. The rotary motion provided by the two motors to the two inboard links may be described as parallel rotary motion inputs. It should be noted that "parallel" is used here to indicate two inputs that are provided independently of one another and not in the geometric sense to indicate the direction of the inputs. In a parallel linkage, the two independent parallel inputs act upon the same body at some distal point where links coupled to the inputs join to drive the same object or link.

A spherical linkage for the purposes of this description is a 3-dimensional version of the 2-dimensional mechanical linkage described above. In the 3-dimensional linkage, all pivot axes pass through a common remote center of spherical rotation. "Pass through" includes axes that may be slightly displaced (due to slight errors in manufacturing of the physical links, for example) from the remote center of spherical rotation to accommodate the structural limitations of the robotic arm where the displacement is small enough that the linkage has substantially the same kinematics (characteristic motions) as if the axes actually included the precise, theoretical remote center of spherical rotation. Note that axes that pass through a remote center of spherical rotation are also perpendicular to a spherical surface centered on the remote center of spherical rotation.

Referring now to the original 2-dimensional linkage of FIG. 7, it will be appreciated that there are two possible positions for each of the inboard links 701, 704 in a five-bar linkage for most of the possible positions of the outboard axis. For example, the inboard link 701 could also be positioned as indicated by the dashed line 701'. This position for the inboard link is generally considered undesirable because the distance between the intermediate axes 714', 711 is reduced and the angle between the outboard links 702', 703 is reduced. It is normally desirable to maximize the distance between the intermediate axes to provide a broad base of support for the outboard axis 715. It is also normally desirable to have the outboard links 702', 703 as close to being at right angles to one another as possible to support the outboard axis 715. While the conventional configuration of a five-bar linkage provides good structural support for the outboard axis 715, the resulting structure requires a substantial amount of space in which to move. The alternative configuration as indicated by the dashed 701', 702' position occupies a smaller area (as projected onto the plane) and is therefore a more compact mechanical configuration.

Figure 8:
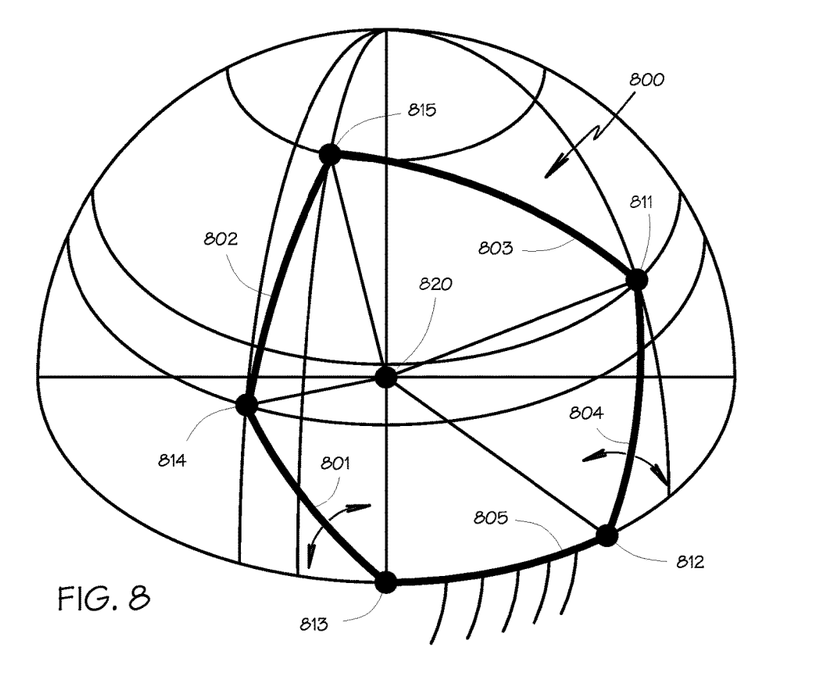
FIG. 8 is a schematic view of a parallel spherical five-bar linkage.

FIG. 8 shows a schematic diagram of a parallel spherical five-bar linkage 800. As with the previously discussed planar five-bar linkage, the parallel spherical five-bar linkage 800 is a system of four rigid links 801, 802, 803, 804 pivoted to each other and to a fixed base or ground link 805. When a parallel five-bar linkage is constructed in a spherical form, all of the pivot axes 811, 812, 813, 814, 815 are perpendicular to a common spherical surface and therefore pass through a remote center of spherical rotation 820 of a sphere. In particular, the outboard axis 815 will always pass through the remote center of spherical rotation 820 within its range of motion. Thus, a parallel spherical five-bar linkage 800 provides the desired constrained motion for a surgical instrument such that the tool shaft of the instrument pivots about a remote center of spherical rotation when supported and moved by the outboard axis 815 of the linkage 800. The motors to move the surgical instrument are placed at the inboard axes 813, 812 of the ground link 805. This avoids the need to move one motor with the other motor as might be required if a serial arm mechanism were used.

Figure 9:
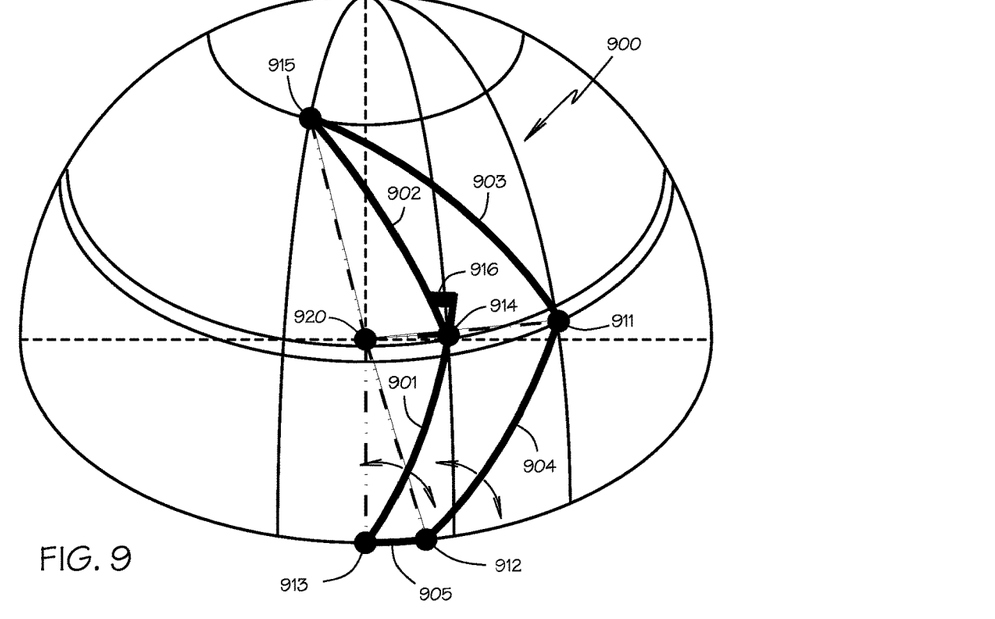
FIG. 9 is a schematic view of another parallel spherical five-bar linkage.

As shown schematically in FIG. 9, it has been discovered that a parallel spherical fivebar linkage 900 can be constrained so that the intermediate axes 914, 911 cannot assume the conventional configuration where the intermediate axes are at their maximum possible separation and, surprisingly, provide good structural support for the outboard axis 915. This results in a more compact configuration that is better suited for use as a robotic arm to support a surgical instrument where it is often necessary to use two or more such arms in close proximity within a limited amount of space as shown by the exemplary system in FIGS. 1-3.

The schematic linkage 900 shown includes a ground link 905, two inboard links 901, 904, and two outboard links 902, 903. The first inboard link 901 includes a first axis of rotation 913 and a first intermediate axis 914 at a first distance from the first axis of rotation. A first outboard link 902 is pivotally coupled to the first inboard link 901 at the first intermediate axis 914. The first outboard link 902 has an outboard axis 915 at a second distance from the first intermediate axis 914.

A mechanical stop 916 may limit the rotation of the first outboard link 902 about the first intermediate axis 914 such that a third distance from the first axis of rotation 913 to the outboard axis 915, when the first outboard link is rotated to the limit of the mechanical stop, is substantially less than the first distance plus the second distance. In another embodiment (not shown), the mechanical stop may be in two parts, each of which limits the rotation of one of the two inboard links.

For links that are simple arcuate segments, such as the links 901-905 shown in FIG. 9, the mechanical stop 916 constrains the motion of the links such that the angle between the first inboard link 901 and the first outboard link 902 is always substantially less than 180 degrees. More generally, the angle between the line segment from the first axis of rotation 913 to the first intermediate axis 914 and the line segment from the first intermediate axis 914 to the outboard axis 915 is constrained to be substantially less than 180 degrees.

A second inboard link 904 has a second axis of rotation 912 at a fourth distance from the first axis of rotation 913 and a second intermediate axis 911 at a fifth distance from the second axis of rotation 912. A second outboard link 903 is pivotally coupled to the second inboard link 904 at the second intermediate axis 911 and to the first outboard link 902 at the outboard axis 915. The outboard axis 915 is at a sixth distance from the second intermediate axis 911. The inventive spherical five-bar linkage is further constrained to have the first and second intermediate axes 914, 911 on the same side of a plane that includes the outboard axis 915 and either of the first 913 or second 912 axis of rotation. This constraint may be achieved by the construction and assembly of the second inboard link 904 and the second outboard link 903.

If the combined length of the second inboard link 904 and the second outboard link 903 is sufficiently long with consideration for the distance between the first axis of rotation 913 and the second axis of rotation 912, the constraint of the motion of the first inboard link 901 and the first outboard link 902 will constrain the second inboard link 904 and the second outboard link 903 to remain in the inventive configuration. For a given length of the first inboard link 901 and the first outboard link 902, a given constraint on the angle between the first pair of links 901, 902, and a given distance between the first axis of rotation 913 and the second axis of rotation 912, there is a maximum distance from the second axis of rotation 912 to the outboard axis 915. If the combined lengths of the second inboard link 904 and the second outboard link 903 is greater than the maximum distance the second pair of links 904, 903 will be constrained to remain in the configuration in which they were assembled with regard to the relative positions of the intermediate axes 914, 911.

The parallel spherical five-bar linkage may be limited in its motion such that the two intermediate axes 914, 911 are relatively close together compared to the maximum separation possible for any given pose of the robotic arm 900. Both the first pair of links 901, 902 and the second pair of links 904, 903 will have the same "handedness." That is, the "elbow" at the intermediate axes 914, 911 for both pairs of links bends to the same side of the arm. The robotic arm 900 thus formed has the characteristic of being either right handed or left handed depending on how the mechanical stop 916 is arranged. The exemplary embodiment shown in FIG. 9 may be considered right handed because the first intermediate joint and the second intermediate joint are maintained on the right side to point in a direction to the right. Likewise, a left handed robotic arm will have the first intermediate joint and the second intermediate joint maintained on the left side to point in a direction to the left. A parallel five-bar spherical linkage constructed according to the above constraints may be described as being limited to a range of compact poses.

As suggested by the embodiment shown in FIG. 9, the robotic arm 900 may be further compacted by making the fourth distance between the first 913 and second 912 axis of rotation substantially less than the distance between the axes on any of the moving links 901, 902, 903, 904.

Figure 10:
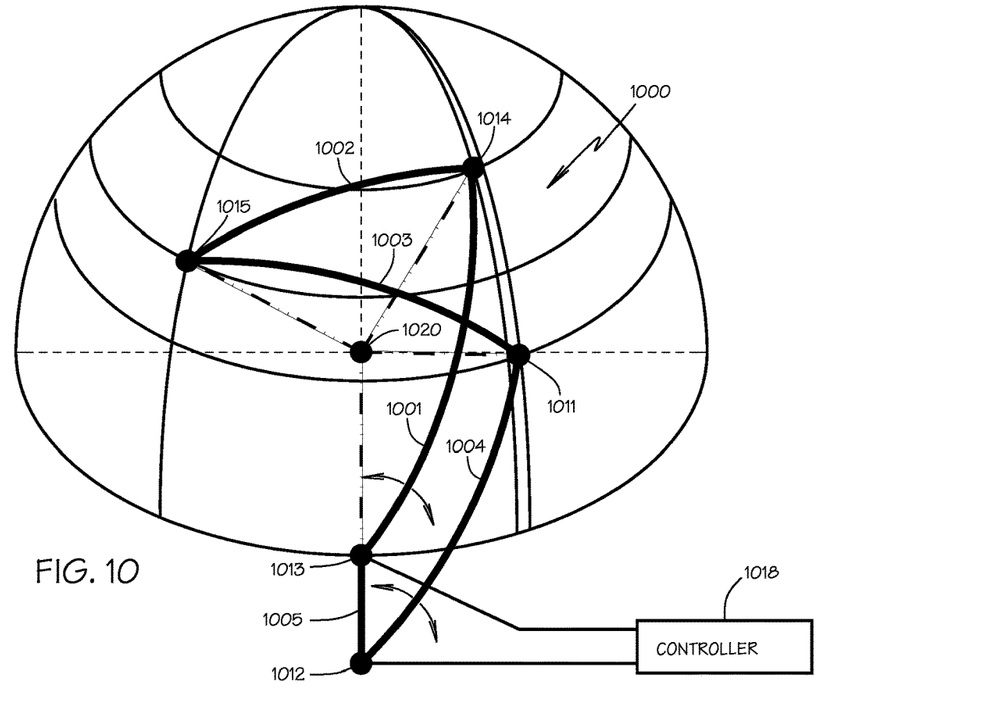
FIG. 10 is a schematic view of another parallel spherical five-bar linkage and a controller.

FIG. 10 shows another embodiment of a parallel spherical five bar linkage 1000 for a robotic arm. The parallel spherical five bar linkage 1000 for the robotic may be still further compacted by arranging the linkage so that the primary range of motion for the outboard axis 1015 is generally on one side of a plane that includes either the first 1013 or second 1012 axis of rotation and the outboard axis 1015.

In some embodiments, such as the embodiment of the parallel spherical five bar linkage 1000 shown in FIG. 10, the first 1013 and second 1012 axis of rotation are driven by motors connected to a controller 1018 to provide signals to the first and second motors. The first motor rotates the first inboard link 1001 and the second motor rotates the second inboard link 1004. The controller 1018 may limit the motion of the inboard links 1001, 1004 such that the first and second intermediate axes 1014, 1011 are on the same side of a plane that includes the outboard axis 1015 and either of the first 1013 or second 1012 axis of rotation. The controller 1018 can provide the same constraint on the range of motion of the links 1001-1004 as the mechanical stop 916 provides for the links 901-904 of the embodiment shown in FIG. 9.

The parallel spherical five bar linkage 1000 may be used to move the outboard axis to a desired position by controllably rotating the inboard links, such as by use of a servo motor or stepper motor. In another embodiment, the parallel spherical five bar linkage 1000 may be used to sense a position of the outboard axis by determining the bearings of the two inboard axes that result from manipulation of the outboard axis. For example, rotary encoders, or other sensors, may be placed at the first 1013 and second 1012 axis of rotation of the parallel spherical five bar linkage illustrated by FIG. 10. The controller 1018 may be replaced by a computer coupled to the two rotary encoders to receive the bearing of each of the inboard links 1001, 1004. The computer may then compute the position of the outboard axis, which may be manipulated by an operator to provide a position input. It will be appreciated that the outboard axis is constrained to rotate about the remote center of spherical rotation 1020 of the spherical linkage. Thus, the parallel spherical five bar linkage may also be used in the control console 122 of FIG. 1 to receive position input for the outboard axis 1015 from the surgeon 120. The position input will have the same constrained motion as the outboard axis of the robotic arm 100.

Figure 11:
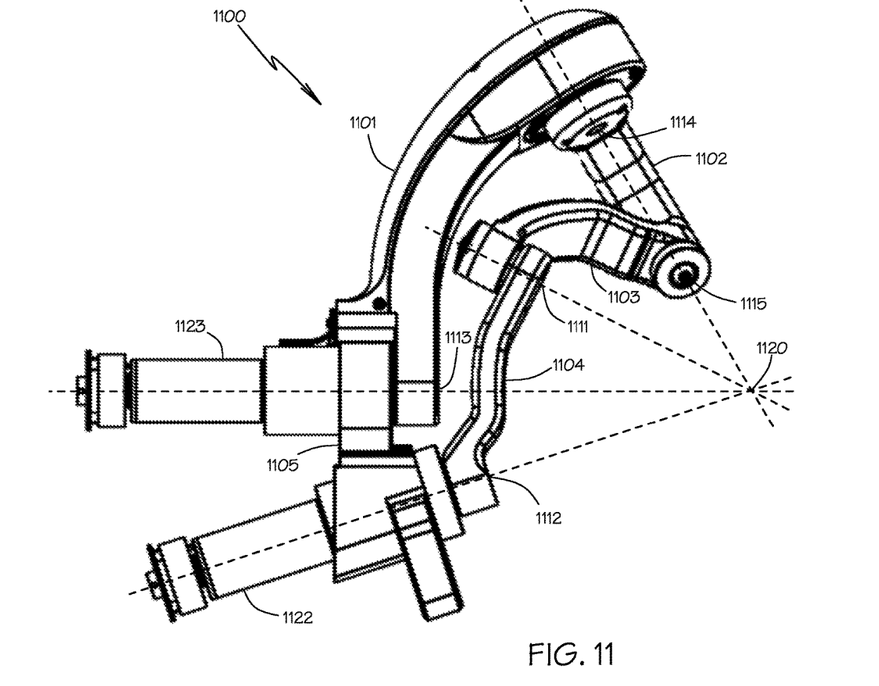
FIG. 11 is a end view of a parallel spherical five-bar linkage.

FIG. 11 shows a parallel spherical five-bar linkage 1100 that embodies the invention that has a structure similar to the robotic arm 100 shown in FIGS. 1-6. The parallel spherical five-bar linkage 1100 is similar in structure and pose to the schematic of the parallel spherical five-bar linkage 1000 of FIG. 10. Five pivot axes 1111-1115, about which the four movable links 1101-1104 rotate, all pass through a common remote center of spherical rotation 1120. The illustrated mechanism includes two motors 1123, 1122 respectively coupled to the first inboard link 1101 and the second inboard link 1104 such that the motors can rotate the links about the first 1113 and second 1112 axes of rotation. The two motors 1123, 1122 are coupled together to form the fifth link 1105, which is the ground link.

The inboard link 1101 is shown as having a generally arcuate form. The remaining three links 1102, 1103, 1104 are shown as having irregular shapes, which may include arcuate segments, to accommodate placement of the pivoted connections 1111, 1114, 1115 such that the links and pivots can pass one another. It will be appreciated that the links may have any desired form without affecting the function of the invention. The linkage will function as a spherical linkage as long as the axes of the pivoted connections 1111, 1112, 1113, 1114, 1115 all pass substantially through a common remote center of spherical rotation 1120.

Figures 12, 13:
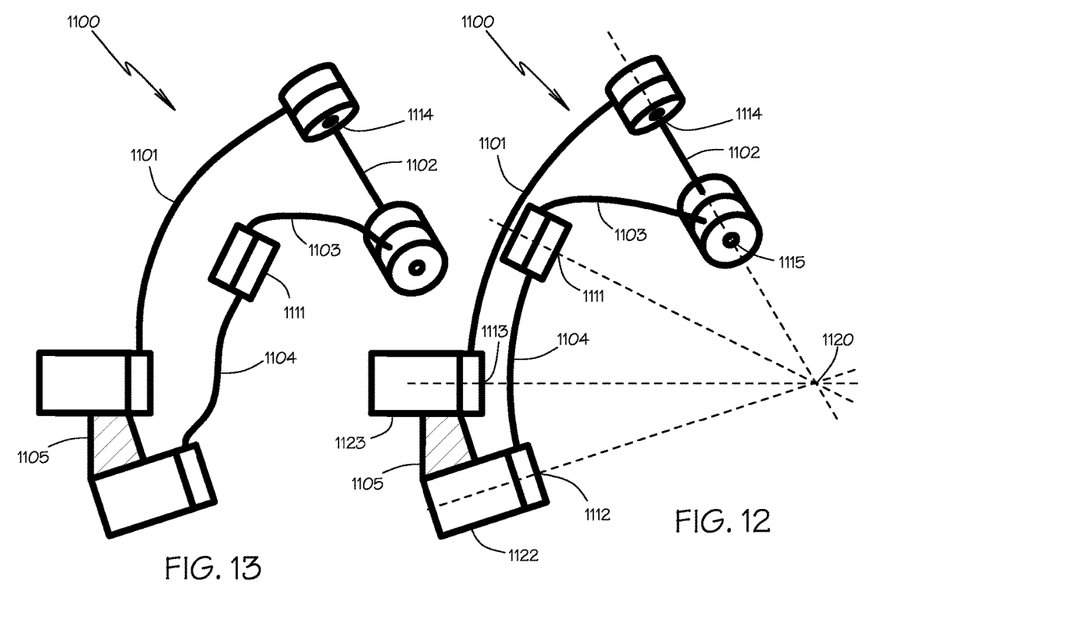
FIG. 12 is a schematic view of the parallel spherical five-bar linkage of FIG. 11.
FIG. 13 is another schematic view of the parallel spherical five-bar linkage of FIG. 11.

FIG. 12 is a schematic representation of the parallel spherical five-bar linkage 1100 of FIG. 11 to show the relationships of the links 1101, 1102, 1103, 1104, 1105 and pivoted connections 1111, 1112, 1113, 1114, 1115 more clearly. FIG. 12 shows the links in an arcuate form to emphasize the spherical nature of the structure. FIG. 13 shows the links in a schematic form that suggests the form of the links in the embodiment of FIG. 11. It may be seen that the irregular shapes of the links shown in FIG. 13 increases the separation between the first pair of links 1101, 1102 and the second pair of links 1104, 1103. It will be appreciated that the form of the links is unimportant as long as they support the pivot axes such that they pass substantially through the remote center of spherical rotation 1120.

In the compact configuration of the inventive parallel spherical five bar linkage, it may be desirable to configure the linkage such that the first pair of links 1101, 1102 coupling the first axis of rotation 1113 to the outboard axis 1115 can freely pass the second pair of links 1104, 1103 coupling the second axis of rotation 1112 to the outboard axis 1115. Since the only requirement of the parallel spherical five-bar linkage is that all the pivot axes pass substantially through the common remote center of spherical rotation 1120, the first pair of links 1101, 1102 and the first intermediate pivot 1114 may be configured so that a first volume swept out by the first pair does not intersect a second volume swept out by the second pair of links 1104, 1103 and the second intermediate pivot 1111. The only connections between the first and second volumes are in the vicinity of the outboard axis 1115 and the ground link 1105. The form of the links in the embodiment illustrated by FIGS. 11 and 13 are an example of a configuration that permits the first pair of links 1101, 1102 to pass the second pair of links 1104, 1103.

Figure 14:
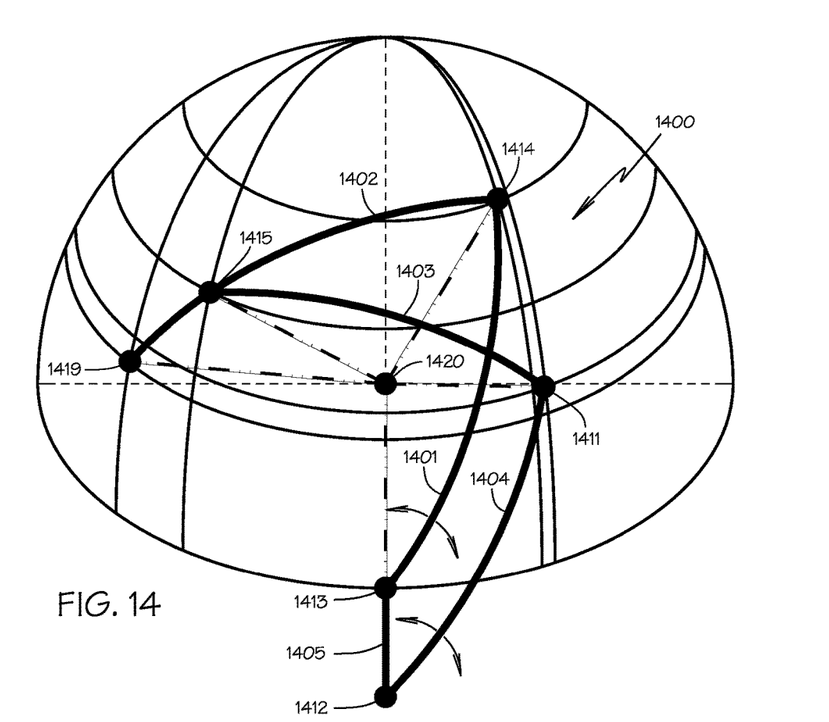
FIG. 14 is a schematic view of another parallel spherical five-bar linkage that includes an insertion axis.

FIG. 14 shows another embodiment of a parallel spherical five-bar linkage 1400 for a robotic arm. In comparison with the linkage 1000 of FIG. 10, the parallel spherical five-bar linkage 1400 includes an outboard link 1402 having an insertion axis 1419 that is spaced apart from the outboard axis 1415 by an offset distance. Ideally the insertion axis 1419 is coincident with the outboard axis 1415. Mechanical packaging advantages can be obtained, however, by separating the insertion axis 1419 from the outboard axis 1415.

Preferably the insertion axis 1419 will be placed on the outboard link 1402 further from the intermediate axis 1414 than the outboard axis 1415. As long as the insertion axis 1419 is perpendicular to the surface of the sphere centered on the remote center of spherical rotation 1420 and therefore passes through the remote center of spherical rotation 1420, then the insertion axis will have the same kinematic characteristics as the pivot axes 1411-1415 of the parallel spherical five-bar linkage 1400. That is, the insertion axis 1419 will move relative to the remote center of spherical rotation 1420. The insertion axis 1419 may or may not lie in the plane defined by the intermediate axis 1414 and the outboard axis 1415.

The placement of the insertion axis 1419 outboard from the pivot axes of the parallel spherical five-bar linkage may allow the surgical tool to be supported and manipulated without interfering with the motion of the linkage 1400. It may also simplify the construction, installation, removal, and sterile boundary construction of cannula 106 and its associated mechanical attachment means.

In some embodiments having a spaced apart insertion axis, such as the one illustrated in FIG. 14, the insertion axis 1419, the outboard axis 1415, and the intermediate axis 1414 may be coplanar. This arrangement may simplify the relationship between the positions of the two inboard links 1401, 1404 and the position of the outboard axis 1415. Note that the insertion axis 1419 can be placed on either of the two outboard links 1402, 1403.

The parallel spherical five-bar linkage of the invention may be described using spherical geometry, which is a plane geometry on the surface of a sphere. While the links of the inventive linkage need not lie of the same spherical surface, or any spherical surface, they can be projected onto a common spherical surface for the purpose of describing the linkage. In spherical geometry, distances may be measured as angles because the geometric relationships on the spherical surface are unaffected by changing the radius of the sphere. Angular distance remains the same regardless of the radius of the sphere.

Navigation on the surface of the Earth is a common example of spherical geometry. Latitude and longitude as used in global navigation are a familiar system for describing locations and directions in a spherical system. The equator defines the points at 0° latitude. The north pole defines 90° latitude and the south pole defines −90° latitude. Longitude is the angular distance on a circle of constant latitude from an arbitrarily defined line of 0° longitude. Longitude is conventionally expressed as being in the range 180° west to 180° east of the 0° longitude line. Bearings are lines of direction from a point expressed as the angle between the bearing and a line of direction to the north pole. The following is a description of an embodiment of the invention expressed in terms of a spherical geometry.

Referring to FIG. 14, the first axis of rotation 1413 of the first inboard link 1401 will be considered as being at 0° latitude and 0° longitude. The second axis of rotation 1412 of the second inboard link 1404 is shown as being at the same longitude and at a negative latitude.

The first intermediate axis 1414 may be spaced apart from the first axis of rotation 1413 by 60°. The first outboard axis 1415 may be spaced apart from the first intermediate axis 1414 by 40°. The insertion axis 1419 may be spaced apart from the outboard axis 1415 by 30°. The second axis of rotation 1412 may be at a fixed position of 0° longitude and 18° negative latitude. It should be remembered that a fixed position means fixed within the frame of reference of the spherical geometry of the linkage and that the entire linkage with its frame of reference may be freely positioned in space. The second intermediate axis 1411 may be spaced apart from the second axis of rotation 1412 by 45°. The second intermediate axis 1411 may be spaced apart from the outboard axis 1415 by 55°.

The range of rotation of the first inboard link 1401 about the first axis of rotation 1413 may be bearings from 80° through −30°. The robotic arm 100 in FIGS. 1-6 is shown with the first inboard link having a bearing of about 15°. The angle between the first inboard link 1401 and the first outboard link 1402 may be from 110° through 30°. The robotic arm 100 in FIGS. 1-6 is shown with an angle of about 75° between the first inboard link and the first outboard link.

These dimension are merely by way of example. The invention may be practiced with linkages having substantially different dimensions and substantially different ranges of motion. The invention is only limited by the claims. It may be desirable to use different dimensions and different ranges of motion to adapt the invention for needs of particular types of surgeries which have particular requirements for the range of motion of the insertion axis and for the space occupied by the device through its range of motion.

Figure 15:
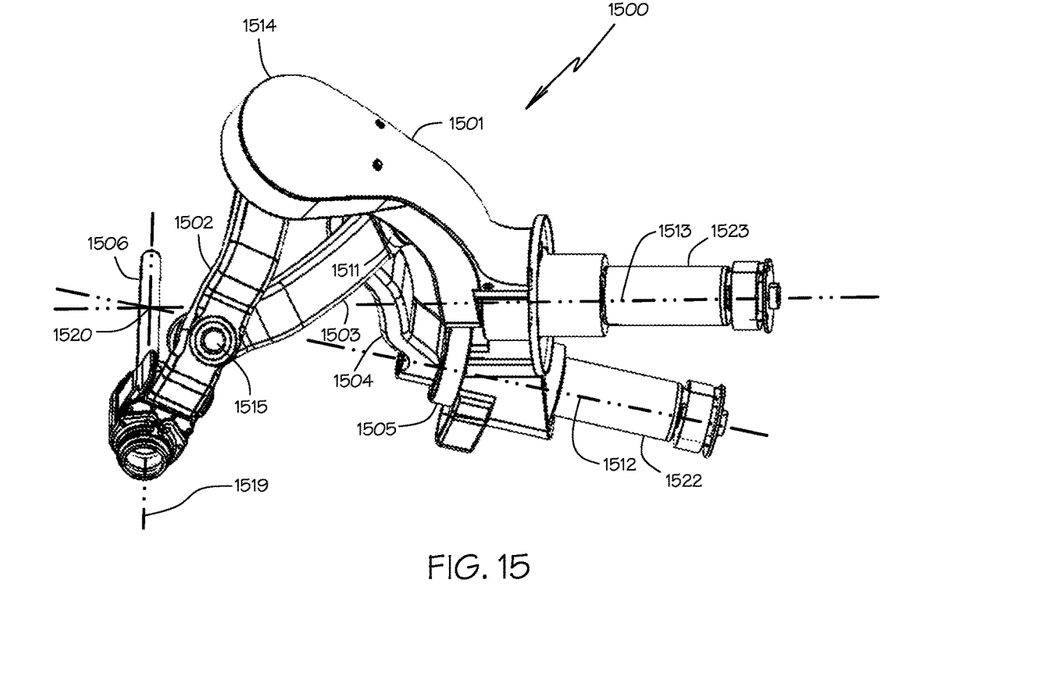
FIG. 15 is a pictorial view of an embodiment of the invention.

FIG. 15 shows an embodiment of a robotic arm 1500 having a geometry that is similar to the schematic geometry of the parallel spherical five-bar linkage 1400 shown in FIG. 14. The view in FIG. 15 is related to the view in FIG. 14 as looking generally from the left toward the right of FIG. 14 to see the view of FIG. 15. The ground link 1505 may be considered to be the proximal end of the robotic arm 1500. A first motor assembly 1523 may be coupled to the ground link 1505 at a first axis of rotation 1513 of the first motor. A second motor assembly 1522 may be coupled to the ground link 1505 at a second axis of rotation 1512 of the second motor separated from the first axis of rotation by a first distance. Note that the axes of rotation 1512, 1513 lie within the motors assemblies 1522, 1523 and that the axes have been drawn as though the motors were transparent so that the relationship of these axes to the structure of the embodiment can be more clearly seen.

Figure 16:
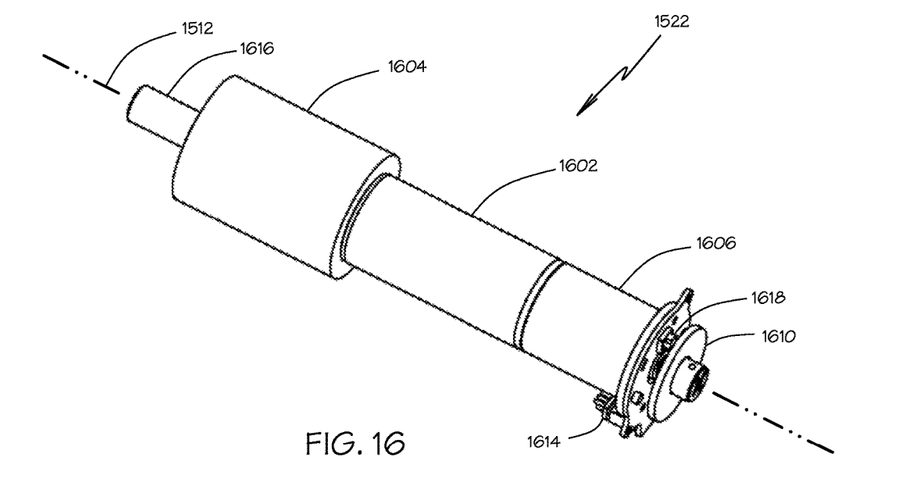
FIG. 16 is a pictorial view of a motor assembly.

FIG. 16 shows a motor assembly 1522 that may be used in an embodiment of a robotic arm. The assembly may include a motor 1602 to provide rotary motion. The motor may be coupled to a shaft 1616 centered on the axis of rotation 1512 of an inboard link through a gearbox 1604 that may reduce the rotation of the motor 1602. A brake 1606 may be coupled to the motor 1602 to stop and hold the motor when it is not moving. An encoder disk 1610 may be coupled to the motor 1602. An optical sensor 1618 may sense the angular motion or position of the encoder disk 1610 and provide a signal on an electrical connector 1614 that may be coupled to a controller for the robotic arm.

A first inboard link 1501 is pivotally coupled to the ground link 1505 at the first axis of rotation 1513. The first inboard link 1501 has a first intermediate axis 1514 at a second distance distal from the first axis of rotation 1513. A first outboard link 1502 is pivotally coupled to the first inboard link 1501 at the first intermediate axis 1514. The first outboard link 1502 has an outboard axis 1515 at a third distance distal from the first intermediate axis 1514. The first outboard link 1502 further includes an insertion axis 1519 spaced apart from the outboard axis 1515 and the intermediate axis 1514. The insertion axis 1519 is at the distal end of the robotic arm 1500. The first outboard link 1502 may support a cannula 1506 that is centered on the insertion axis 1519. Note that the insertion axis 1519 passes through the cannula 1506 and that the insertion axis has been drawn as though the cannula was transparent so that the relationship of the insertion axis to the axes of rotation and the structure of the embodiment can be more clearly seen.

Figure 17:
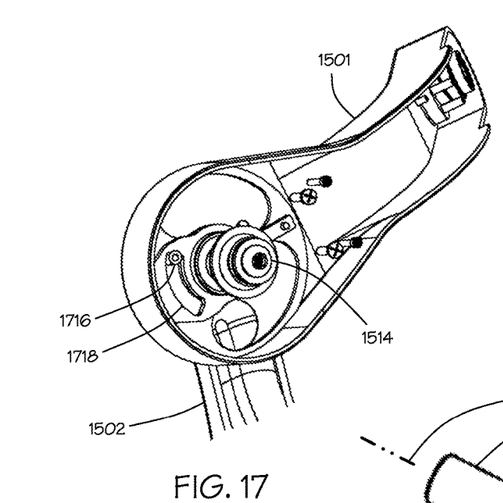
FIG. 17 is a pictorial view of a detail of the embodiment of FIG. 15.

As shown in FIG. 17, a constraint may limit the rotation of the first outboard link 1502 about the first intermediate axis 1514. The maximum extent of the variable distance between the first axis of rotation 1513 at which the first motor 1523 is coupled to the ground link 1505 and the outboard axis 1515 is constrained to be substantially less than a sum of the distance from the first axis of rotation 1513 to the first intermediate axis 1514 and from first intermediate axis 1514 to the outboard axis 1515. FIG. 17 shows a detail of the first intermediate axis 1514 that pivotally couples the first inboard link 1501 to the first outboard link 1502. A stop pin 1716 may be coupled to the first outboard link 1502 such that it moves with the first outboard link. A slot 1718 may be provided on the first inboard link 1501 within which the stop pin 1716 is constrained, thus limiting the rotation of the first outboard link 1502 about the first intermediate axis 1514.

A second inboard link 1504 is pivotally coupled to the ground link 1505 at the second axis of rotation 1512. The second inboard link 1504 has a second intermediate axis 1511 at a fifth distance distal from the second axis of rotation 1512. A second outboard link 1503 is pivotally coupled to the second inboard link 1504 at the second intermediate axis 1511. The second outboard link 1503 is also pivotally coupled to the first outboard link 1502 at the outboard axis 1515, thus closing the parallel spherical five bar linkage. All of the pivotal axes of the parallel spherical five bar linkage pass through the remote center of spherical rotation 1520. The first 1514 and second 1511 intermediate axes are on the same side of a plane that includes the outboard axis 1515 and either of the first 1513 or second axis of rotation 1512, which are collocated with the first 1523 and second 1522 motors. If the first 1514 and second 1511 intermediate axes are viewed as elbows, both elbows remain bent in the same direction throughout the constrained range of motion of the robotic arm 1500.

It is to be understood that the inventive parallel spherical five-bar linkage may be embodied in both powered and unpowered configurations. In powered embodiments, devices such as servo motors rotate the inboard links. The parallel spherical five-bar linkage translates those rotations into two dimensional movement of the outboard axis. In unpowered embodiments, two dimensional movement of the outboard axis is translated by the parallel spherical five-bar linkage into rotations of the inboard links. Devices such as rotary encoders may sense the bearings of the inboard links and that information may be used to compute the position of the outboard axis. Constraining the rotation of an intermediate axis as previously described is advantageous in unpowered embodiments because the constraint limits the position of the outboard axis to one of the two possible positions that correspond to the bearings of the inboard links.

Figure 18:
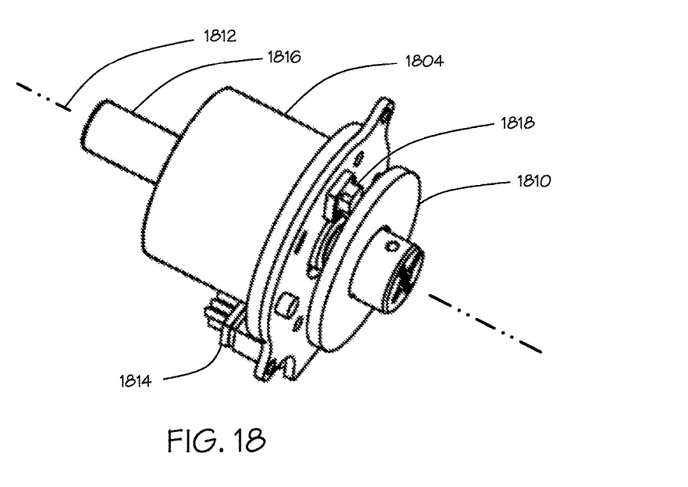
FIG. 18 is a pictorial view of an optical encoder.

FIG. 18 shows an encoder assembly that may be used in an unpowered embodiment of a parallel spherical five bar linkage. A position of the outboard axis may be sensed by determining bearings of the two inboard axes of the parallel spherical five bar linkage that result from manipulation of the outboard axis. An encoder disk 1810 may be coupled to a shaft 1816 centered on the axis of rotation 1812 of each of the two inboard links of the parallel spherical five bar linkage. The encoder disk 1810 may be coupled through a gearbox 1804 that may increase the rotation of the encoder disk. An optical sensor 1818 may sense the angular motion or position of the encoder disk 1810. The optical sensor 1818 may provide a signal on an electrical connector 1814. The signals from the two rotary encoders may be coupled to a computer to determine the bearing of each of the inboard links.

The computer may determine the position of the outboard axis from the two bearings. It should be noted that there will generally be two possible positions for the outboard axis for a given pair of bearings of the inboard links. The computer may be provided with the range of the rotation of one of the outboard links about the intermediate axis as limited by a constraint. The additional input of the range of rotation may allow the computer to uniquely determine the position of the outboard axis.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Instead, the embodiments of the invention should be construed according to the claims that follow below.

What is claimed is:

1. A robotic arm for a minimally invasive surgical system, the robotic arm comprising:
a parallel five-bar spherical linkage that includes
a ground link having a first end and an opposing second end,
a first pair of links pivotally coupled at a first intermediate joint and coupled at a first end of the first pair of links to the first end of the ground link, and
a second pair of links pivotally coupled at a second intermediate joint, coupled at a first end of the second pair of links to the second end of the ground link, and coupled at a second end of the second pair of links to a second end of the first pair of links to form an outboard joint,
the parallel five-bar spherical linkage having a range of compact poses in which the first pair of links and the second pair of links in the parallel five-bar spherical linkage have only a same handedness, the parallel five-bar spherical linkage configured to spherically rotationally move a robotic surgical tool coupled to the parallel five-bar spherical linkage about a remote center of spherical rotation; and
a constraint configured to limit the parallel five-bar spherical linkage to only the range of compact poses.

2. The robotic arm of claim 1, wherein:
the robotic arm includes a first motor and a second motor to provide two parallel rotary motion inputs to the parallel five-bar spherical linkage; and
the constraint is a controller coupled to the first motor and the second motor to pose the five-bar spherical linkage in only the range of compact poses.

3. The robotic arm of claim 1, wherein the constraint includes a mechanical stop coupled to a joint in the parallel five-bar spherical linkage to limit the parallel five-bar spherical linkage to only the range of compact poses.

4. The robotic arm of claim 1, wherein the constraint includes a mechanical stop on each of two parallel rotary motion inputs to limit the parallel five-bar spherical linkage to only the range of compact poses.

5. The robotic arm of claim 1:
wherein the first intermediate joint and the second intermediate joint are on a same side of a plane that includes the outboard joint, one end of the ground link, and the remote center of spherical rotation.

6. The robotic arm of claim 1, wherein the ground link of the parallel five-bar spherical linkage is configured to be coupled to a table to support the robotic arm over a patient.

7. The robotic arm of claim 1, wherein the ground link of the parallel five-bar spherical linkage is configured to be coupled to a set-up arm to support the robotic arm over a patient.

8. A robotic arm for a minimally invasive surgical system, the robotic arm comprising:
a parallel five-bar spherical linkage means for spherically rotationally moving a robotic surgical tool about a remote center of spherical rotation, the parallel five-bar spherical linkage means including
a ground link having a first end and an opposing second end,
a first pair of links pivotally coupled at a first intermediate joint and coupled at a first end of the first pair of links to the first end of the ground link, and
a second pair of links pivotally coupled at a second intermediate joint, coupled at a first end of the second pair of links to the second end of the ground link, and coupled at a second end of the second pair of links to a second end of the first pair of links to form an outboard joint,
the parallel five-bar spherical linkage means moving within a range of compact poses in which the first pair of links and the second pair of links in the parallel five-bar spherical linkage have only a same handedness;
means for limiting the parallel five-bar spherical linkage means to only the range of compact poses.

9. The robotic arm of claim 8, wherein:
the robotic arm includes means for providing two parallel rotary motion inputs to the parallel five-bar spherical linkage; and
the means for limiting is configured to limit the means for providing two parallel rotary motion inputs to posing the five-bar spherical linkage means in only the range of compact poses.

10. The robotic arm of claim 8, wherein the means for limiting includes a mechanical stop coupled to a joint in the parallel five-bar spherical linkage to limit the parallel five-bar spherical linkage to only the range of compact poses.

11. The robotic arm of claim 8, wherein the means for limiting includes a mechanical stop on each of two parallel rotary motion inputs to limit the parallel five-bar spherical linkage to only the range of compact poses.

12. The robotic arm of claim 8:
wherein the first intermediate joint and the second intermediate joint are on a same side of a plane that includes the outboard joint, one end of the ground link, and the remote center of spherical rotation.

13. The robotic arm of claim 12, wherein the ground link of the parallel five-bar spherical linkage means is configured to be coupled to a table to support the robotic arm over a patient.

14. The robotic arm of claim 12, wherein the ground link of the parallel five-bar spherical linkage means is configured to be coupled to a set-up arm to support the robotic arm over a patient.

* * * * *